United States Patent [19]
Mowlai-Ashtiani

[11] Patent Number: 6,110,182
[45] Date of Patent: Aug. 29, 2000

[54] TARGET SOCKET

[75] Inventor: Ali Mowlai-Ashtiani, Cincinnati, Ohio

[73] Assignee: Ohio Medical Instruments Company, Inc., Cincinnati, Ohio

[21] Appl. No.: 09/337,242

[22] Filed: Jun. 22, 1999

Related U.S. Application Data

[60] Provisional application No. 60/090,162, Jun. 22, 1998.

[51] Int. Cl.[7] ....................................................... A61B 6/03
[52] U.S. Cl. .............................. 606/130; 606/1; 600/417; 600/429
[58] Field of Search ...................................... 606/108, 130, 606/1; 604/93, 117, 174, 173, 178, 180; 600/407, 427, 429, 426, 411, 417, 414

[56] References Cited

U.S. PATENT DOCUMENTS

| | | |
|---|---|---|
| 4,805,615 | 2/1989 | Carol . |
| 4,955,891 | 9/1990 | Carol . |
| 5,116,345 | 5/1992 | Jewell et al. . |
| 5,529,358 | 6/1996 | Dinkler et al. ............................ 600/233 |
| 5,695,501 | 12/1997 | Carol et al. ............................... 606/130 |
| 5,810,712 | 9/1998 | Dunn ......................................... 600/174 |
| 5,891,157 | 4/1999 | Day et al. ................................. 606/130 |
| 5,891,158 | 4/1999 | Manwaring et al. .................... 606/130 |
| 5,961,456 | 10/1999 | Gildenberg ............................... 600/429 |
| 5,971,997 | 10/1999 | Guthrie et al. ........................... 606/130 |
| 5,984,930 | 11/1999 | Maciunas et al. ....................... 606/130 |

OTHER PUBLICATIONS

William D. Tobler, MD, D.; Scott Basham, RN, *Frameless Stereotaxy for the Aspiration of Intracerebrel Hematomas*, Mayfield Clinic & Spine Institute, 1997.

Neil Dorward, F.R.C.S., et al., *Clinical Paper –Clinical Introduction of an Adustable Rigid Instrument Holder for Frameless Stereotactic Interventions*, Computer Aided Surgery 2:180–185, Wiley–Liss, Inc. 1997.

Flyer, *Mayfield/Acciss An Interactive, Image–Guided Stereotactic Planning and Navigation System*, OMI Surgical Products, a Division of Ohio Medical Instrument Company, Inc. Copyright 1996.

*Primary Examiner*—Gene Mancene
*Assistant Examiner*—Pedro Philogene
*Attorney, Agent, or Firm*—Wood, Herron & Evans L.L.P.

[57] ABSTRACT

A target socket for frameless stereotactic surgery has a ring with an arcuate band that captures a target ball therein. The ring defines a pair of spaced apart channels which provide the ring with a degree of flexibility. The ring defines a radially oriented gap extending throughout the ring's entire thickness, the gap being spanned by a tightening member which allows a user to easily manually tighten the ring upon a target ball held within the arcuate band. The target socket is also provided with an attachment element for attaching the target socket to a surgical tooling structure. The attachment element has at least three links to provide the target socket with at least six degree of freedom.

18 Claims, 2 Drawing Sheets

TARGET SOCKET

This application claims benefit to U.S. provisional application 60/090,162 filed Jun. 22, 1998.

FIELD OF THE INVENTION

This invention relates to neurosurgical apparatus generally, and more particularly, to a target socket for use in neurosurgery.

BACKGROUND OF THE INVENTION

Freehand localization and biopsy of small, deep-seated, intracranial targets, often in discreet and sensitive areas, can be very difficult and unsafe. However, it has been possible to define and correlate the position of single or multiple points within the cranium with preoperative imaging and by the use of stereotactic frames known in the art. One known technique helps define the position of an intracranial target by coordinates derived from a frame that is rigidly fixed to the skull during preoperative MRI or CT imaging and during the surgical procedure.

More recent technological advances have led to the development of image guidance systems that do not require frame-based coordinates for target localization. One such "frameless" stereotactic guidance system is the MAYFIELD/ACCISS Stereotactic Workstation which is commercially sold the assignee of this application.

Frameless systems provide constant intraoperative navigational information, which permits a surgeon to identify precisely the spacial position of a hand-held probe in the surgical field with reformatted CT or MRI shown on a high definition display monitor. Unlike stereotactic head frames, therefore, these frameless systems allow the surgeon to locate multiple targets in different spacial planes.

The localization of an intracranial target with a stereotactic frame is achieved by advancing a probe along a predetermined linear trajectory that is usually fixed directly to the patient's skull. Systems do not carry structure fixed to the patient's head. Therefore, in using a hand-held localizing probe, much more of the steadiness dependent on the surgeon's hand. For this reason, fixed trajectory target sockets have been devised. These devices allow a surgical instrument to be introduced to intracranial target along a stable and fixed trajectory. The trajectory remains fixed relative to the intracranial target during the procedure, thus eliminating the risk of misdirection or drift associated with freehand procedures.

One such device is shown in assignee's U.S. Pat. No. 5,810,712, which is expressly incorporated by reference herein. One of this device includes of a target ball with a centrally axially drilled hole, the target ball being locked in a fixed position with, for example, a pair of hinged plates defining holes in which the target ball is sandwiched. Once the target ball hole is aligned with the intracranial target, the plates are tightened upon the target ball so that a surgical instrument may be inserted through the target ball hole and proceed along its fixed trajectory to the intracranial target.

Another such device for fixing the trajectory of the surgical instrument for intracranial procedures is the MAYFIELD/ACCISS AccuPoint targeting sphere available from the assignee of the present invention. In this system, a generally circular frame receives a targeting sphere therein, the targeting sphere then being locked upon a desired trajectory by a plurality of screws. These screws are introduced into the frame via threaded screw bores, wherein each screw must be independently tightened upon the targeting sphere before the targeting sphere is securely fixed in space so that a surgical instrument may be introduced along the desired trajectory. The MAYFIELD/ACCISS system is supported in space via a connecting arm to a Budde®-Halo retractor, which defines a work station above a patient's head.

However, while these prior art devices have proved suitable for many types of surgery, there is room for improvement. For example, when using multiple screws, each of which must be tightened separately upon the target ball, during tightening, upon the target ball there is a possibility the desired trajectory may become offset slightly from the desired trajectory. It is therefore desirable to be able to secure a target ball in space in such a manner so that a desired trajectory to an intracranial target is maintained during the act of tightening the target ball in place, with a reduced potential for "play" during tightening.

Also, in prior art devices, it is difficult and time consuming to loosen the target ball from its fixed position, re-position the target ball to a new desired trajectory, and then tighten the target ball on its new desired trajectory. Therefore, it is also desirable to be able to easily tighten and loosen the target ball in order to change trajectories more quickly and easily in the relatively cramped spaces of a surgical operating room.

SUMMARY OF THE INVENTION

These and other problems of previously known target sockets are overcome by a target socket in accordance with the principles of the present invention. The target socket of the present invention includes an annular ring of generally uniform radial thickness having an outer surface and an inner surface. The ring has a radially oriented gap between spaced apart open end portions and at least two radially oriented channels formed in the outer surface of the ring that are spaced away from the gap by substantially equal angular intervals. The inner surface of the gap defines an arcuate band to receive a target ball that may be fixed in place relative to the annular ring.

The target socket has a tangentially oriented tightening member spanning the gap between the end portions of the ring to selectively vary the width of the gap, thereby selectively varying the radius of the arcuate band. The target ball received within the arcuate band may be fixed in place by manually turning the tightening member, thereby crimping the arcuate band closed upon the target ball. Alternatively, the target ball may be rotated relative to the ring while held within the arcuate band while the tightening member is loosened. The radially oriented channels provide ring flexibility so as to allow the ring to close upon the target ball held within the arcuate band in response to manual manipulation of the tightening member.

The target socket also has an attachment element with first and second ends. The first end secures to the ring and the second secures to a surgical tooling structure. The attachment element has at least three serially connected links and at least two hand manipulable connectors which variably hold the links in fixed relation to each other with star-burst engagement surfaces. The attachment element provides at least six degrees of freedom to enable selectively locating the ring relative to the surgical tooling structure.

In a preferred embodiment, the surgical tooling structure is an arcuate hollow retractor having an arcuate track, the second end of the attachment member being fixable to and movable along the arcuate track.

These and other objects and advantages of the present invention will become more readily apparent during the following detailed description, together with the drawings herein.

DETAILED DESCRIPTION OF THE PREFERRED EMBODIMENT

Figure 2:
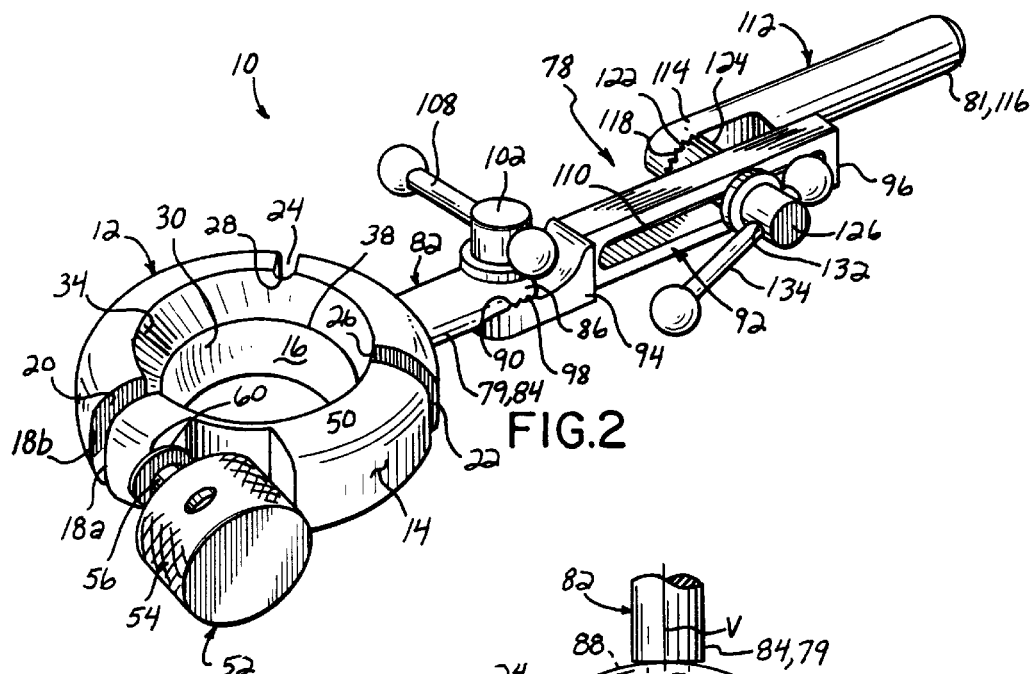
FIG. 2 is a perspective view of the target socket in accordance with the first preferred embodiment of the invention.
Figure 3:
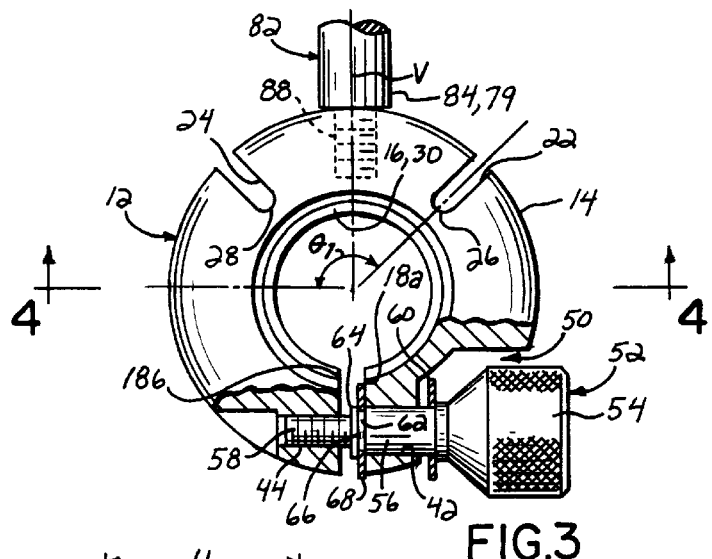
FIG. 3 is a top view of the target socket partially broken away.
Figure 4:
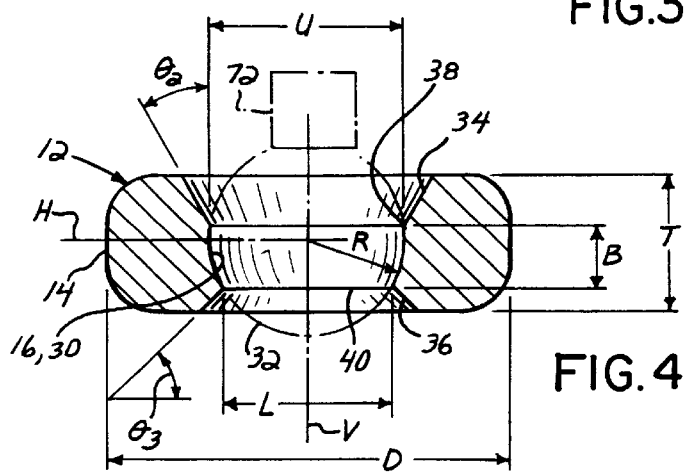
FIG. 4 is a cross-sectional view of the target socket taken along line 4—4 of FIG. 3.

As seen in FIGS. 2–4, the target socket 10 of the present invention is generally a ring 12 with an outer surface 14, an inner surface 16, and having a thickness T. The ring 12 has a central vertical axis V and a medial horizontal axis H. The ring 12 has confronting end portions 18a, 18b which define a radially oriented gap 20 extending from the inner surface 16 through to the outer surface 14 throughout the ring's entire thickness T.

The ring 12 is made from aluminum by a CNC lathing process known in the art. While the target socket is made of aluminum in the preferred embodiment, it will be understood by those in the art that other materials suitable for use in a sterile surgical environment also be used.

The ring 12 defines first and second channels 22, 24 located at generally equal angular intervals from the gap 20. The channels 22, 24 are oriented so as to extend radially outwardly from the center of the ring 12. The channels 22, 24 extend from the rings outer surface 14 toward, but do not communicate with the ring's inner surface 16.

In order to maintain the structural integrity of the ring 12, the channels 22, 24 are formed so as to leave walls 26, 28 that will not easily permanently deform under repeated use while, at the same time, allow a user to easily manipulate the target socket 10, as discussed further below.

Figure 1:
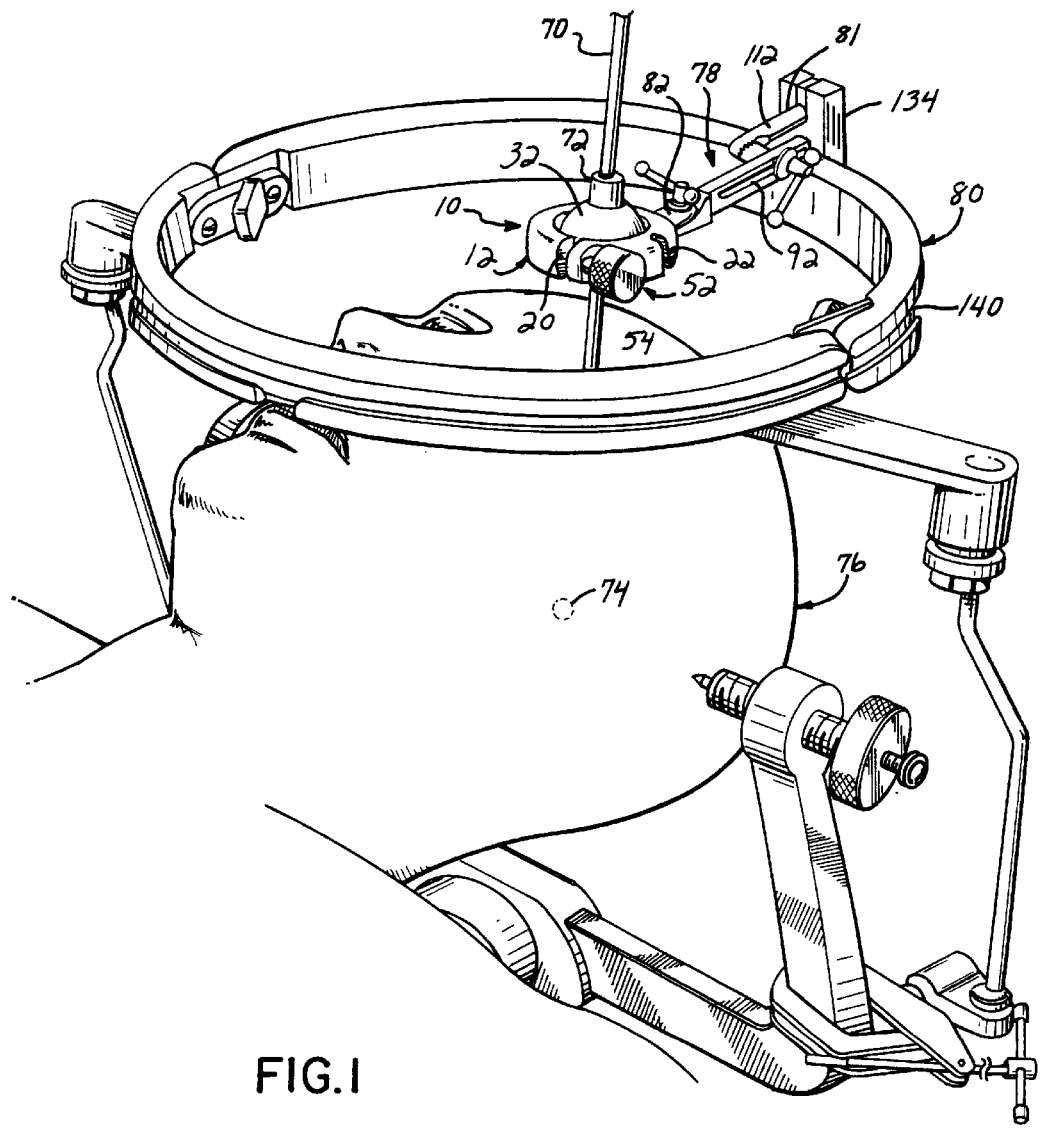
FIG. 1 is a perspective, environmental view which shows use of a target socket for a surgical instrument, in accordance with a first preferred embodiment of the invention.

The inner surface 16 of the ring 12 defines an arcuate band 30 in which a target ball 32 is located, as seen in FIGS. 1 and 4. The arcuate band 30 has an upper edge diameter U is about the same as the target ball 32 so when the target ball 32 is fixed in position a user needs only to apply a small amount of force to close the arcuate band 30 upon the target ball 32.

The ring 12 has an upper chamfer surface 34 and a lower chamfer surface 36 which abut respective upper and lower edges 38, 40 of the arcuate band 30. As will be discussed further below, the upper and lower chamfer surfaces 34, 36 accommodate the desired range of motion of a surgical instrument 70 located in the target ball 32.

The ring 12 defines a pair of first and second coaxial bores 42, 44 communicating with respective end portions 18a, 18b. Each bore 42, 44 extends tangentially in relation to the ring 12, so as to communicate with the ring outer surface 14 proximate the gap 20. A cut-out region 50 defined in the outer surface 14 accommodates insertion and manual manipulation of a tightening member 52 having a knob 54 and a shaft 56 with a threaded end 58. In a preferred embodiment, the second bore 44 is threaded so as to receive the threaded end 58 of the tightening member 52.

In a preferred embodiment, the knob 54 is knurled to provide texture to allow a user to more easily grasp and manipulate the tightening member 52. A washer 60 is placed on the tightening member 52 and located between the knob 54 and the outer surface 14 in order to prevent metal fatigue that could otherwise be caused by engagement of the knob 54 against the outer surface 14. The shaft 56 has a step 62 approximately halfway between the knob 54 and the threaded end 58. The step 62 and a circumferential flange 64 raised on the shaft 56 define a groove 66 in which a lock washer 68 is seated. When the threaded end 58 of the shaft 56 is threadedly engaged with the second bore 44, the lock washer 68 seated in the groove 66 is located between the confronting end portions 18a, 18b. The lock washer 68 helps resist the tightening member 52 from disengaging the threaded end 58 from the second bore 44.

In a preferred embodiment, the ring 12 has an outside diameter D of about 1.98 inches and has a thickness T along the central vertical axis V of about 0.72 inches. The gap 20 and the channels 22, 24 are about 0.125 inches wide. The channels 22, 24 are about 0.365 inches deep. Each channel 22, 24 is located at respective angular intervals $\theta_1$ of about 135° from the gap. The upper chamfer surface 34 defines an angle $\theta_2$ of about 30° from the central vertical axis V. The lower chamfer surface 36 defines an angle $\theta_3$ of about 45° from the central vertical axis V. The arcuate band has a radius R of about 0.501 inches and a height B of about 0.29 inches. The cut out region 50 is about 0.365 inches deep. The tightening member 52 is about 1.5 inches long and the knob 54 has a diameter of about 0.75 inches.

As is best seen in FIG. 1, the target socket 10 captures the target ball 32 therein to be variably locked in place to accurately and precisely position a surgical instrument 70, for example, a viewing probe or an aspirator, in relation to an intracranial target 74. The standard size of a target ball 32 known in the art is one inch in diameter and is manufactured to very tight specifications. in a preferred embodiment, the gap 20 in the target socket 10 need not be widened by manipulating the tightening member 52 in order to accommodate the target ball 32. The target ball 32 simply snaps into place within the arcuate band 30. The upper edge 38 of the arcuate band 30 has a diameter U of about 1.000 inches, and the lower edge 40 of the arcuate band 30 has a diameter L of about 0.857 inches. So, the target ball 32 is captured in the arcuate band 30 from above and the diameter L of the lower edge 40 of the arcuate band 30 prevents the target ball 32 from releasing downwardly through the ring 12.

Before manipulating the tightening member 52 to secure the target ball 32 in a desired position, a surgical instrument carrier 72 is fixedly attached to the target ball 32. Because the instrument carrier 72 rises above the target ball 32, the upper chamfered surface 34 provides a greater range of motion as the target ball 32 and instrument carrier 72 are manipulated side to side within the arcuate band 30 to allow the surgical instrument 70 inserted therein to be accurately aligned with the target 74 within a patient's skull 76. Likewise, the lower chamfered surface 36 provides the surgical instrument 70 with a range of motion as the target ball 32 is manipulated side to side within the arcuate band 30.

In a preferred embodiment, to provide a greater degree of targeting freedom to a user, the target socket 10 is provided with an attachment element 78 that is attached at a first end 79 to the ring 12 and is variably attached at a second end 81 to a target halo 80. U.S. Pat. No. 5,529,358, showing a target halo 80, is incorporated herein in its entirety by reference. The attachment element 78 has a first link 82 with first and second ends 84, 86. The first end 84 is attached to the ring 12 about halfway between the channels 22, 24. The ring 12 defines a link bore 88 into which the first end 84 is seated by means known in the art. The first link 82 has a first starburst engagement surface 90 proximate the second end 86. The first link 82 defines an unthreaded bore (not shown) at about the center of the first starburst surface 90.

A second link 92, having first and second link ends 94, 96, has a second starburst engagement surface 98 proximate the first end 94. The second link 92 defines a threaded bore (not shown) at about the center of the second starburst surface 98. The first and second starburst surfaces 90, 98 are received against each other and may be variably locked in position by a threaded bolt 102 received through the unthreaded bore and threaded into the second link threaded bore. The bolt 102 defines a through bore (not shown) in which a sliding dumbbell handle 108 is journaled so that the bolt 102 may be easily manually manipulated. The dumbbell handle 108 allows a user to more easily manually tighten and loosen the first link 82 relative to the second link 92 in the confines of surgical work space, thus providing for a first degree of target socket 10 freedom of movement relative to the ring's horizontal plane H (FIG. 4).

The second link 92 defines a channel 110 in which a third link 112 is variably fixed. The third link 112 has a first end 114 and a second end 116. The first end 114 has a starburst engagement surface 118. A threaded bore (not shown) is defined in the third link 112 at about the center of the starburst surface 118. The starburst surface 118 is received against a threadless nut 124 having a starburst engagement surface 122. The nut 124 has a channel portion (not shown) that is received in the channel 110 so that when the nut 124 is loosened it may be variably slid within the channel 110, providing a second degree of freedom. A second bolt 126 has a washer (not shown) carried thereon and is received through the nut 124 seated in the slot 110 and threads into the third link bore. The second bolt 126 defines a through bore 132 in which a dumbbell handle 134 is carried so that the third link 112 may be variably fixed relative to the second link 92, providing a third degree of freedom.

In a preferred embodiment, the attachment element 78 is variably fixed at its second end 81 to a clamp 138 that travels in an arcuate channel 140 defined in the surgical halo 80 positioned above the patient's skull 76. The target socket 10 is thereby provided with a fourth degree of freedom, rotating axially relative to the clamp 138. The target socket 10 is provided with a fifth degree of freedom, whereby the third link 113 may be variably fixed along its length within the clamp 138. The target socket 10 is provided with a sixth degree of freedom, whereby it may be variably fixed in position relative to the surgical halo 80 as the clamp 138 is slid around and variably fixed within the arcuate channel 135.

In use, the target socket 10 may be employed for any procedure requiring frameless stereotactic. For example, the target socket 10 may be used for the frameless stereotactic for the aspiration of intracerebral hematomas. Prior to the procedure, patient specific images from MRI and CT scans can be viewed for target 74 identification and optimal trajectory planning. External markers (not shown) are placed upon the patient for most accurate patient/target registration. The target socket 10 is attached to the surgical halo 80 via the clamp 134. The target socket holds the target ball 32, therein. The surgical instrument carrier 72 is fixed to the target ball 32 and the surgical instrument 70 is attached to the instrument carrier 72. The surgical instrument 70 is linked to a computer workstation (not shown) which carries the data and imaging from the preoperative MRI and CT scans. Multiplanar orthogonal and non-orthogonal, and three-dimensional views of the intracerebral hematoma is viewed at the computer workstation to determine a suitable cerebral entry point and trajectory.

An entry point is determined to create a trajectory that takes advantage of the long axis of the hematoma. The most dependent and deepest portion of the hematoma is selected as the target 74. In order to optimally stabilize the surgical instrument 70, i.e., a rigid side port aspirating biopsy cannula, the target socket 10 is positioned over the entry point by using the six degrees of freedom to manipulate the target socket 10 relative to the target 74 and fix the target socket 10 in position relative to the surgical halo 80.

It is not necessary to determine the exact coordinates of the target in frameless stereotactic procedures, since once the target socket 10 is positioned, the surgeon manipulates the surgical instrument 70 and target ball 32 within the arcuate band 30 of the ring 12. Once the proper trajectory is determined at the computer workstation, the surgeon manipulates the tightening member 52 to secure the target ball 32 within the arcuate band 30 along that desired projectory. A twist drill hole or burr hole is made in the skull 76 at the predetermined trajectory entry point. The surgical instrument 70 is then passed through to the stereotactic target 74 along the fixed desired trajectory.

While the present invention has been illustrated by the description of a preferred embodiment, and while the embodiment has been described in considerable detail, it is not the intention to restrict or in any way limit the scope of the appended claims to such detail. Additional advantages and modifications will readily appear to those skilled in the art. For example, the widths of the gap and channels may be wider or narrower. The location of the channels relative to the gap may be varied as desired. Or, the cutout region accommodating the tightening member knob may be eliminated. The invention in its broadest aspects is therefore not limited to the specific details and illustrative examples shown and described. Accordingly, departures may be made from such details without departing from the spirit or scope of the general inventive concept.

What is claimed is:

1. A target socket for a surgical instrument comprising:
    an annular ring of generally uniform radial thickness and having an outer surface and an inner surface, the ring having a radially oriented gap defined by spaced open end portions and also having at least two radially oriented channels defined in the outer surface and spaced away from the gap, the inner surface being shaped in an arcuate band; and
    a tangentially oriented tightening member spanning the gap between the end portions of the ring and selectively movable relative to the ring to vary the space of the gap, thereby to selectively vary the radius of the arcuate band, whereby a target may be held fixed in place within the arcuate band or may be rotated relative to the ring while still held within the arcuate band, the at least two radially oriented channels providing flexibility for the ring to open and close upon the target in response to movement of the member.

2. The target socket of claim 1 wherein the member threadably connects to at least one of the open end portions of the ring and the member is rotatable relative to the ring to affect variation in the spacing of the gap.

3. The target socket of claim 1 wherein the member has an internal end residing within a first of the open end portions and an opposite external end located adjacent a second of the open end portions, the external end being manipulable to move the member relative to the ring to vary the spacing of the gap.

4. The target socket of claim 3 wherein the outer surface of the ring includes a radially outwardly opening cutout region, and the external end of the member resides generally within the cutout region.

5. The target socket of claim 3 wherein the external end of the member comprises a knob.

6. The target socket of claim 1 wherein each of the channels has a radial dimension greater than one half of the radial thickness of the ring.

7. The target socket of claim 1 wherein the channels are located opposite the gap.

8. The target socket of claim 1, further comprising:
an attachment element having a first end secured to the ring and a second end securable to a surgical tooling structure, the attachment element including at last three serially connected links and at least two hand manipulable connectors, each of the connectors residing generally between and interconnecting at least two links, each connector including opposing star-burst engagement surfaces and a manually rotatable handle for manually engaging/disengaging the starburst surfaces to fixedly secure/unsecure the respective links relative to each other to prevent/permit relative movement of the links, the attachment element providing at least six degrees of freedom to enable selective locating of the ring relative to the surgical tooling structure.

9. The target socket of claim 8 wherein the surgical tool structure is an arcuate halo retractor having an arcuate track, and the second end of the attachment member is movable along and fixable to the arcuate track.

10. A combination target socket and target comprising:
an annular ring of generally uniform radial thickness and having an outer surface and inner surface, the ring having a radially oriented gap residing between spaced open end portions and also having at least two radially oriented channels formed in the outer surface and spaced away from the gap, the inner surface being shaped in an arcuate band;
a tangentially oriented tightening member spanning the gap between the end portions of the ring and selectively moveable relative to the ring to vary the space of the gap, thereby to selectively vary the radius of the arcuate band for holding the target fixedly in place within the arcuate band for allowing the target to be rotated relative to the ring while still held within the arcuate band, the at least two radially oriented channels providing flexibility for the ring to open and close upon the target in response to movement of the member; and a target removably held within the arcuate band of the ring, the target being fixable/rotatable relative to the arcuate band depending on the position of the tightening member, the target adapted to receivably hold a surgical instrument.

11. The target socket of claim 10 wherein the member threadably connects to at least one of the open end portions of the ring and the member is rotatable relative to the ring to affect variation in the spacing of the gap.

12. The target socket of claim 10 wherein the member has an internal end residing within a first of the open end portions and an opposite external end located adjacent a second of the open end portions, the external end being manipulable to move the member relative to the ring to vary the spacing of the gap.

13. The target socket of claim 12 wherein the outer surface of the ring includes a radially outwardly opening cutout region, and the external end of the member resides generally within the cutout region.

14. The target socket of claim 12 wherein the external end of the member comprises a knob.

15. A surgical tool holding structure comprising:
an arcuate halo retractor ring having an arcuate track;
an attachment member having internal and external ends, an external end movable along and securable to the arcuate track, thereby to extendably position the internal end inside the halo retractor;
a target socket fixed to the internal end of the attachment member, target socket having an annular ring having an outer surface and an inner surface, the ring having a radially oriented gap residing between spaced open end portions and also having at least two radially oriented channels formed in the outer surface and spaced away from the gap, the inner surface being shaped in an arcuate band and a tangentially oriented tightening member spanning the gap between the end portions of the ring and selectively moveable relative to the ring to vary the space of the gap, thereby to selectively vary the radius of the arcuate band; and
a target removably held within the arcuate band of the ring, the target being fixable/rotatable relative to the arcuate band depending on the position of the tightening member, the target adapted to receivably hold a surgical instrument.

16. In combination, the tool holding structure of claim 15 and further comprising:
a surgical instrument held within the target.

17. The invention of claim 16 wherein the surgical instrument is a viewing probe.

18. The invention of claim 16 where the surgical instrument is an aspirator.

* * * * *